(12) United States Patent
Blount

(10) Patent No.: US 6,197,263 B1
(45) Date of Patent: Mar. 6, 2001

(54) AUTOMOBILE AIR FRESHENER

(76) Inventor: Eugene D. Blount, 4433 Corinth Dr., Dayton, OH (US) 45410

( * ) Notice: Subject to any disclaimer, the term of this patent is extended or adjusted under 35 U.S.C. 154(b) by 0 days.

(21) Appl. No.: 09/236,018

(22) Filed: Jan. 22, 1999

(51) Int. Cl.[7] .................................................. A61L 9/00
(52) U.S. Cl. ........................ 422/125; 422/123; 392/390; 392/391
(58) Field of Search .................. 422/4, 5, 120, 422/123–125, 305, 306, 307; D23/366; 392/386, 390, 391; 55/385.1, 385.3; 239/57, 60; 261/DIG. 17, DIG. 65; 307/43, 46, 64, 65, 80

(56) References Cited

U.S. PATENT DOCUMENTS

| | | | | |
|---|---|---|---|---|
| D. 314,044 | * | 1/1991 | Montanari | D23/366 |
| 4,325,108 | * | 4/1982 | Spingler | 362/183 |
| 4,808,347 | * | 2/1989 | Dawn | 261/DIG. 65 |
| 4,968,456 | * | 11/1990 | Muderlak et al. | 261/DIG. 65 |
| 5,126,078 | | 6/1992 | Steiner et al. | 422/124 |
| 5,220,269 | * | 6/1993 | Chen et al. | 320/2 |
| 5,250,265 | * | 10/1993 | Kawaguchi et al. | 422/5 |
| 5,373,581 | | 12/1994 | Smith | 392/390 |
| 5,394,506 | * | 2/1995 | Stein et al. | 392/390 |
| 5,407,642 | * | 4/1995 | Lord | 422/5 |
| 5,422,078 | * | 6/1995 | Colon | 422/124 |
| 5,432,882 | * | 7/1995 | Glynn | 392/390 |
| 5,478,505 | * | 12/1995 | McElfresh et al. | 422/124 |
| 5,649,317 | * | 7/1997 | Suzuki | 455/345 |
| 5,788,931 | | 8/1998 | Quintana | 422/125 |
| 5,977,656 | * | 11/1999 | John | 307/43 |
| 5,979,175 | * | 11/1999 | Ellison | 455/351 |

* cited by examiner

Primary Examiner—Robert J. Warden, Sr.
Assistant Examiner—Theresa T. Snider
(74) Attorney, Agent, or Firm—Edward L. White

(57) ABSTRACT

The invention is an air freshener for use in automobiles, having a base-power unit and a detachable fragrance dispersing unit. The fragrance dispersing unit has a heating element disposed therein and is adapted to receive standard replaceable gel-scent cartridges. The detachable fragrance dispersing unit can be attached to an automobile vent system to utilize the vehicle's air moving system to disperse the fragrance throughout the automobile. The power supply in the base-power unit allows a user to select between drawing power from a cigarette lighter plug, a battery disposed within the base power unit, or a solar electric cell disposed on the outer surface of the base power unit.

2 Claims, 3 Drawing Sheets

AUTOMOBILE AIR FRESHENER

CROSS REFERENCE TO RELATED APPLICATIONS

None.

I. BACKGROUND OF INVENTION

1. Field of the Invention

The invention is an air freshener for use in automobiles, having a base-power unit, and a connectable and detachable ventilate fragrance dispersing unit containing a heating element and a replaceable gel-scent cartridge, the fragrance dispersing unit having a detachable means to attach the fragrance dispersing unit to the automobile vent system to utilize the automobile air-conditioning system to disperse the fragrance throughout the automobile. The power supply in the base-power unit may be a cigarette lighter plug, a battery or a solar/electric cell.

2. Description of Prior Art

The use of air fresheners in known in prior art, some adapted for use in automobiles. An air freshener for motor vehicles of a type inserted in an electric cigarette lighter socket included in the dash of an automobile, including an airflow casing for holding a replaceable scent cartridge and a heat producing resistor is disclosed in U.S. Pat. No. 5,788,931 to Quintana, incorporated herein by reference. In U.S. Pat. No. 5,373,581 to Smith, incorporated herein by reference, an automobile plug-in air freshener is disclosed, inserted into the cigarette lighter socket in an automobile, having a rotatable switch, a heating element, replaceable scent cartridges and a formed slot for inserting the cartridges. U.S. Pat. No. 5,126,078 to Steiner, et al., incorporated herein by reference, discloses an air freshener dispenser having a two-part housing comprising a base having a control circuit, and a cover having the dispensing blower and replaceable fragrance cartridge, the invention powered by onboard battery supply and having a low battery alarm mechanism.

The present invention is distinguished from the above in that it has a variety of power sources, including solar power, has at least two detachable components, including a base-power unit and a ventilated fragrance dispersing unit having a heating element for thermally transforming a gel contained in a replaceable cartridge to an airborne vaporous scent. The two components are connected by a retractable wire. The ventilated fragrance dispersing unit may be separated from the base-power unit and attached to the vent port in the air-conditioning system of the automobile, allowing the air conditioning of the automobile to act as a means of dispersing the fragrance from the cartridge throughout the interior of the automobile. A switch included on the base power unit allows the user to choose the power source, which is either solar/voltaic cell, low-voltage dry cell battery, or the automobile electrical system.

II. SUMMARY OF THE INVENTION

It is an object of the present invention to provide an automobile air freshener having two main detachable components, including a base-power unit and a fragrance dispersing unit. The fragrance dispersing unit has a heating element for thermally transforming a fragrant gel contained in a replaceable cartridge to an airborne vaporous scent. The fragrance dispersing unit is connected to the base-power unit by an insulated low-voltage wire, preferably flexible, and either detachable on both the fragrance dispersing unit and base-power unit or retractable within the base-power unit.

It is a further object of the invention to provide a fragrance dispersing unit which is ventilated and may be separated from the base-power unit for attachment to the vent port in the air-conditioning system of the automobile, allowing the air conditioning of the automobile to assist in dispersing the vaporous scent from the heated cartridge throughout the interior of the automobile.

It is also an object of the invention to provide a low voltage wire which is extended when the units are separated and when the units are reconnected, the wire is retracted by a means contained within the base-power unit. The base-power unit is conformed to be securely inserted into the cigarette lighter socket of the automobile, thus deriving its power source from the automobile electrical system. The base-power unit also contains a low-voltage dry cell battery chamber allowing the invention to be powered by onboard battery power, or its power source may be derived from a solar cell included into the base-power unit when the base-power unit is attached to a window by a means of attachment. A switch included on the base power unit allows the user to choose the power source.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited, in this application, to the details of construction and to the arrangements of the components set forth in the following description or illustrated in the drawings. The invention is capable of other embodiments and of being practiced and carried out in various ways. Also, it is to be understood that the phraseology and terminology employed herein are for the purposes of description and should not be regarded as limiting. As such, those skilled in the art will appreciate that the conception, upon which this disclosure is based, may readily be utilized as a basis for the designing of other structures, methods, and systems for carrying out the general purposes of the present invention. Additional benefits and advantages of the present invention will become apparent to those skilled in the art to which the present invention relates from the subsequent description of the preferred embodiment and the appended claims, taken in conjunction with the accompanying drawings. It is important, therefore that the claims be regarded as including and of such equivalent constructions insofar as they do not depart from the spirit and scope of the present invention.

Further, the purpose of the foregoing abstract is to enable the United States Patent and Trademark Office and the public, generally, and especially the scientists, engineers and practitioners in the are who are not familiar with patent or legal terms or phraseology, to quickly determine from a cursory inspection, the nature and essence of the technical disclosure of the application. The abstract is neither intended to define the invention of the application which is measured by the claims, nor is it intended to be limiting as to the scope of the invention in any way.

III. DESCRIPTION OF THE DRAWINGS

IV. DESCRIPTION OF THE PREFERRED EMBODIMENT

Figure 1:
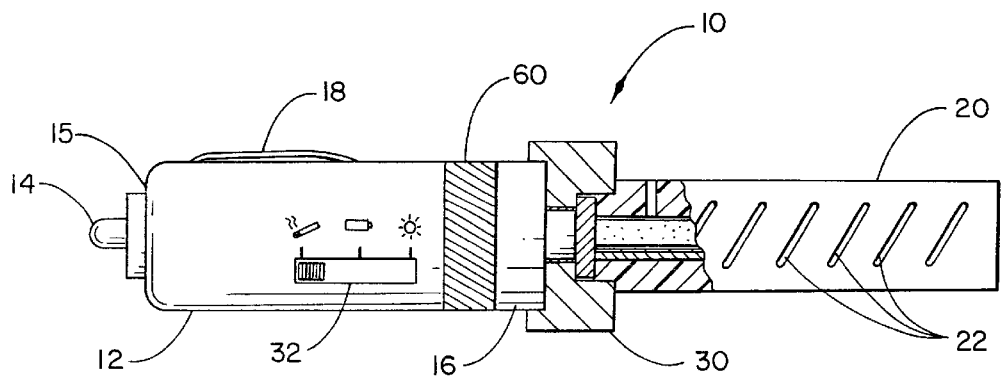
FIG. 1 is a side view of the invention with connected components.
Figure 2:
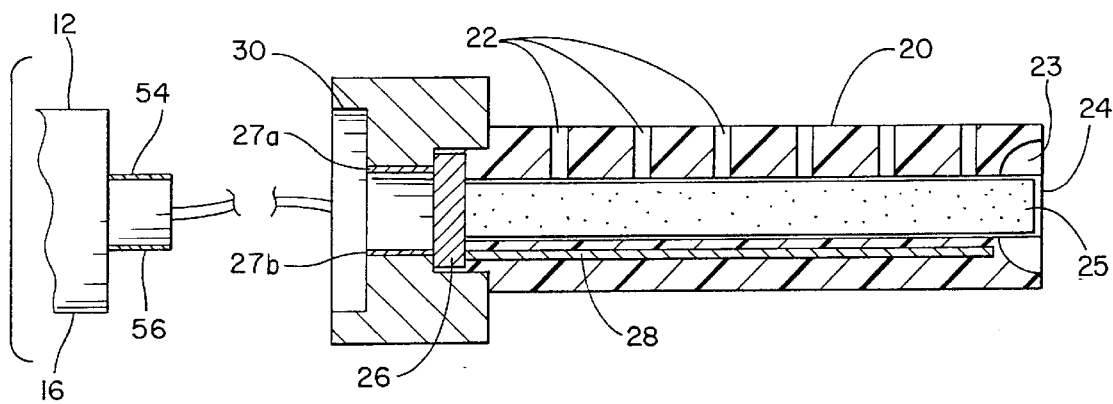
FIG. 2 is a side view of the fragrance dispersing unit separated from the base-power unit.

Referring now to the drawings, where like numerals represent like parts, the invention, as shown in FIGS. 1–6 of the drawings, is an automobile air freshener 10 having a base-power unit 12 and a ventilated fragrance dispersing unit 20. The base-power unit 12 and the ventilated fragrance dispersing unit 20 are detachably connected to each other for use as a single unit, or as two separated units.

Figure 4:
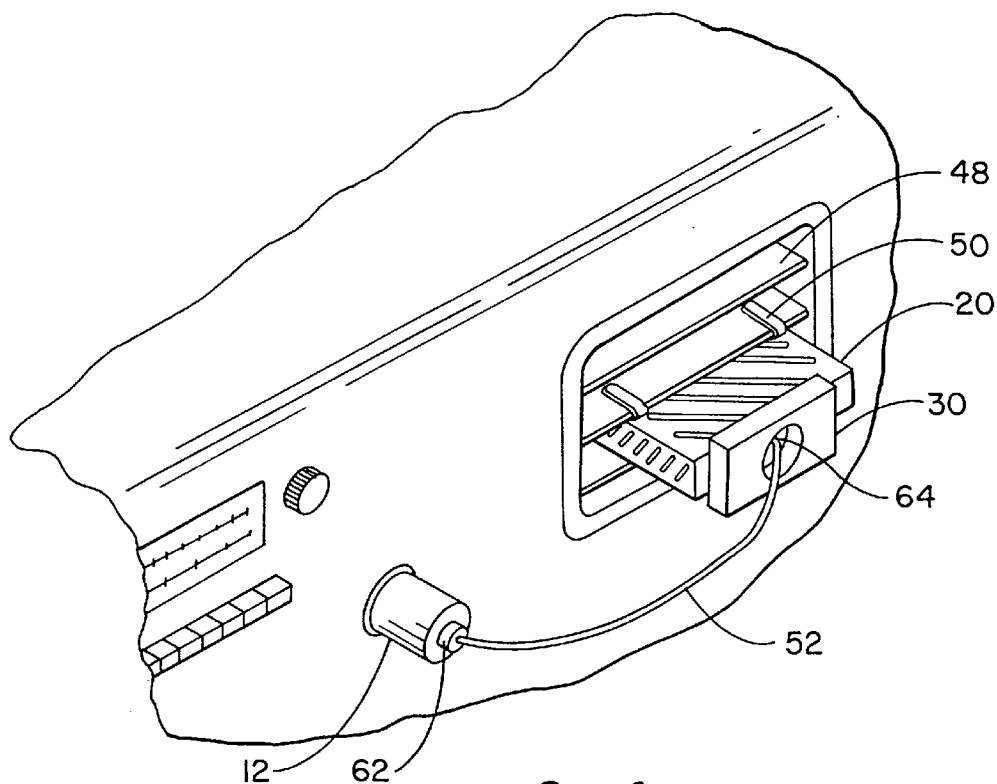
FIG. 4 is a side view of the fragrance dispersing unit attached to a vent port of an automobile and the base-power unit inserted within the cigarette lighter socket.
Figure 5:
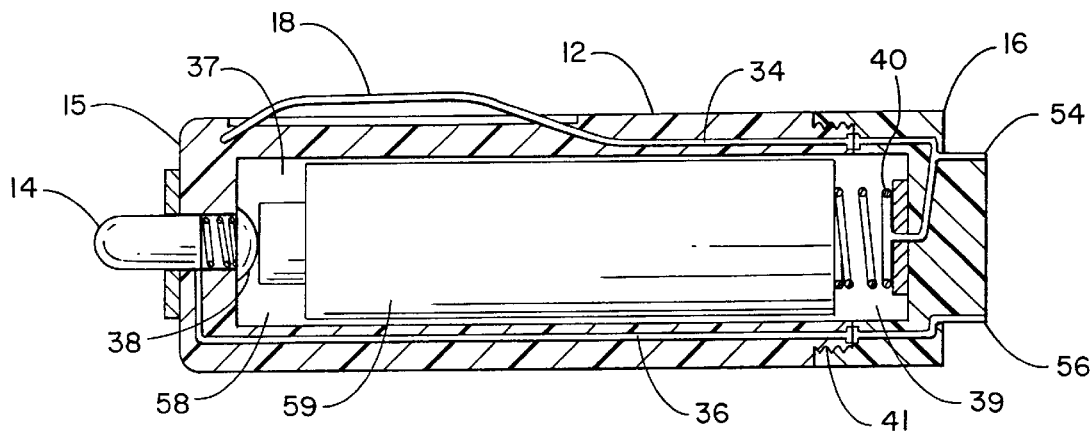
FIG. 5 is a cross-section of the base unit.

The base-power unit 12, as shown in FIGS. 1–2 and 5–6 of the drawings, is formed to be removably inserted into a conventional cigarette lighter socket in most automobiles, as shown in FIG. 4, and has a socket end 15 and a male connector end 16. The socket end 15 is inserted into the cigarette lighter socket of an automobile. Located in a central proximity to the socket end 15 is an electrically conductive spring loaded socket cathode contact 14 which is intended to meet the positive contact point in the cigarette lighter socket of the automobile for a positive current to the base-power unit 12. An electrically conductive resilient socket anode contact 18 is also provided on the base-power unit 12 to lie in contact with an inner surface of the cigarette lighter socket of the automobile, providing a negative current or ground to the base-power unit 12. Referring now to FIG. 5, the male connector end 16 has on opposing sides an exposed electrically conductive singular anode terminal 54 connected to the socket anode contact 18 by a negative lead 34 and an exposed singular electrically conductive cathode terminal 56 connected to the socket cathode contact 14 by a positive lead 36. The negative lead 34 and positive lead 36 are also made of electrically conductive material.

In the event that the user does not choose to use a cigarette lighter socket to obtain the operational power source, the base-power unit 12 has a battery cavity 58 suitable to removably contain a low-voltage dry cell battery 59. The base-power unit is provided with a means 41 to access the battery cavity 58 for replacement of the dry cell battery 59 upon its expiration. In a preferred embodiment, the means 41 of access is a screw cap at the male connector end 16.

The battery cavity 58 has at a primary end 37 corresponding to the socket end 15 of the base-power unit 12, a battery cathode contact 38 positioned within the cavity 58 at a location positioned to contact with the positive point of the dry cell battery 59 contained within the cavity 58. At a secondary end 39 of the battery cavity 58 corresponding to the male connector end 16 of the basepower unit 12 is a battery anode contact 40, positioned within the cavity 58 at a location to come into contact with the negative point of the dry cell battery 59 contained within the cavity 58. The battery anode contact 40 is connected to the aforementioned negative lead 34, and the battery cathode contact 38 is connected to the positive lead 36.

In the event that the user does not choose a battery power source or use of the cigarette lighter socket to power the invention, a solar cell 60 producing electro-voltaic current is affixed to the base-power unit 12, with the positive lead connected 36 to the positive current supply of the solar cell and the negative lead 34 connected to the negative current supply of the solar cell 60. As shown, the solar cell 60 is attached to the base power unit 12. Alternatively, the solar cell could be attached thereto by a wire (now shown) so that the solar cell could be placed on the dash while the base unit 12 remains plugged into the cigarette lighter socket.

Figure 6:
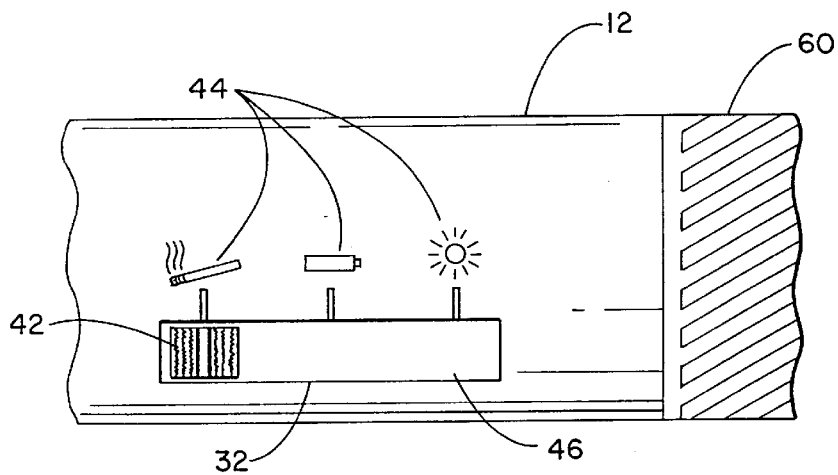
FIG. 6 is a close-up of the power selector switch.

A power selector switch 32, as shown in FIGS. 1 and 6 of the drawings, is included in the base-power unit 12. The power selector switch 32 allows the user to select the power source from the three sources previously mentioned: a cigarette lighter source, battery source 59, or solar cell source 60. This power selector switch 32 includes a slide slot 46, a slide switch 42 slidably engaged with the slide slot 46, and symbolic power source indicators 44 imprinted above the slide slot 46 on the base-power unit 12. If the slide switch 42 is positioned in indicated alignment with one of the three symbolic power indicators 44, that selected power source is activated to the exclusion of the other two power sources. It is recommended that if the solar power source is chosen, the invention be placed or positioned at a location where the sun or other adequate light source is exposed to the solar cell 60 in order to provide enough electro-voltaic current to operate the invention 10.

The fragrance dispersing unit 20, as shown in FIGS. 1–4 of the drawings, has a multiplicity of vent slots 22 which allow for free flow of air throughout the unit 20, yet not affecting a rigid integrity of the component unit 20. The fragrance dispersing unit 20 is hollow, defining a longitudinal cartridge slot 24 therein of an internal dimension to accept standard gel-scent cartridges 25 currently available on the market. Finger indentations 23 in the ventilated fragrance unit allow for easier removal of standard scent cartridges 25. The cartridge slot 24 has an indentation 23 to allow the user to grip a portion of the gel-scent cartridge 25 for insertion and retrieval of the cartridge. The vent slots 22 allow for a flow of air through the fragrance dispersing unit 20 onto the gel surface of the gel-scent cartridge 25. On one end of the fragrance dispersing unit 20, a female connector end 30 is presented, which is conformed to closely accept the male connector end 16 of the base-power unit 12. Within the female connector end 30 are electrically conductive heating element contacts 27a and 27b, connected to a low-voltage electric heating element 26. When the base-power unit 12 and the fragrance dispersing unit 20 are connected, the anode terminal 54 and the cathode terminal 56 on the male connector end 16 of the base-power unit 12 contact the heat element contacts 27a, 27b of the female connector end 30 of the fragrance dispersing unit 20. The selected power supply provides low-voltage electrical current to the heating element 26, causing the heating element 26 to become warmer than the ambient air surrounding the invention due to electrical resistance. This heat is transferred to a heat dispersing plate 28, which is positioned within the cartridge slot 24 in a parallel plane to the gel-fragrance cartridge 25, and in close proximity to the gel-fragrance cartridge 25. As the heat dispersing plate 28 becomes warmer, the heat is transferred to the gel-fragrance cartridge 25 to cause a thermal conversion of the gel within the gel fragrance cartridge 25 to a vaporous aroma, such vaporous aroma being transferred through the vent slots 22 in the fragrance dispersing unit 20. The heat generated by the electric heat element 26 and heat dispersing plate 28 should be enough to thermal degenerate the gel in the gel-fragrance cartridge 25, but not enough to cause deformation or destruction of the components of the invention, nor cause harm to the user.

Figure 3:
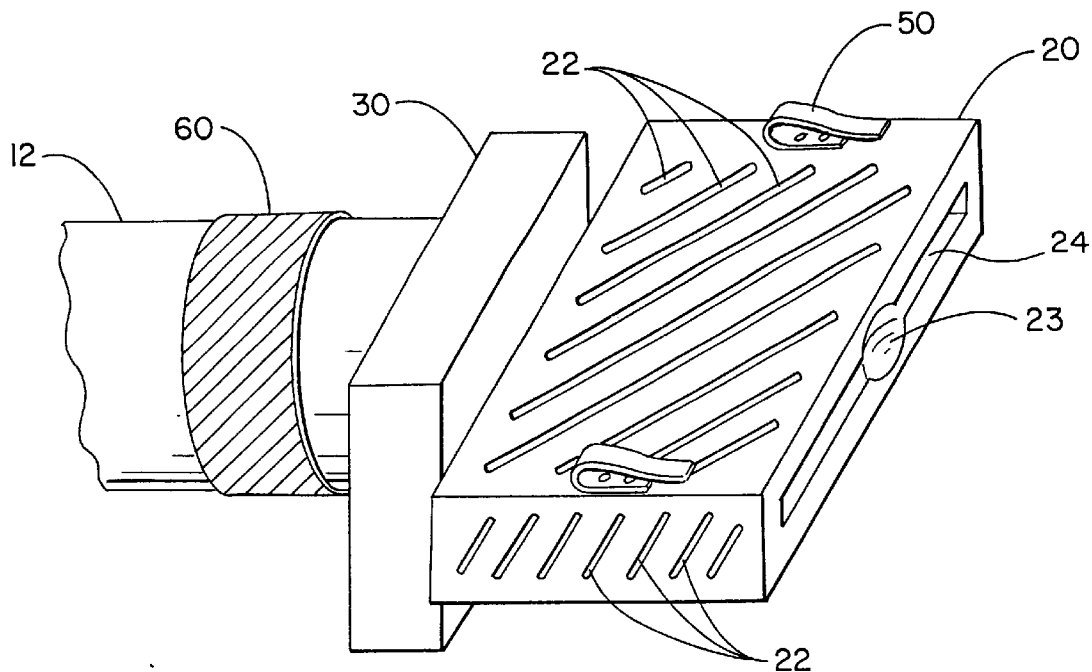
FIG. 3 is a perspective view of the invention with the components connected.

Attached to the fragrance dispersing unit 20 is a resilient vent clip, 50 as shown in FIGS. 3–4 of the drawings, which allows the fragrance dispersing unit 20 to be attached to a typical automobile vent port 48 of the air-conditioning system. The resilient vent clip 50 should be made of a material which is strong enough to securely attach the fragrance dispersing unit 20 to the automobile vent port 48, but prevent marring or destruction of the automobile vent port 48. Attachment of the fragrance dispersing unit 20 to the vent port 48 of the automobile allows the air conditioning system of the automobile to assist in the distribution of the vaporous aroma throughout the interior of the automobile.

Figure 7:
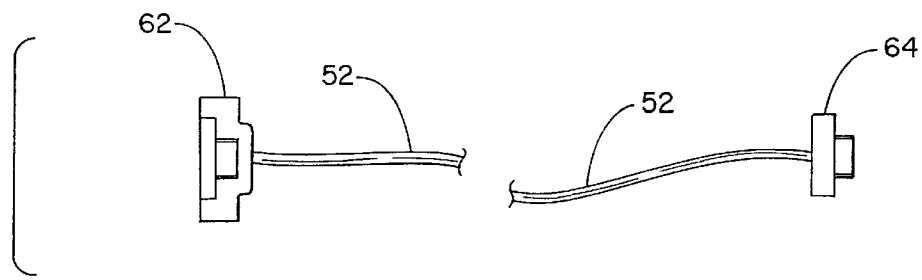
FIG. 7 is a view of the connector wire.

When the base-power unit 12 and the fragrance dispersing unit 20 are separated, a connecting wire 52, as shown in FIGS. 4 and 7 of the drawings, may be utilized to electrically connect the two units together. This would be commonly use when the base-power unit 12 is powered by its insertion in the cigarette lighter socket and the fragrance dispersing unit 20 is attached to the automobile vent port 48. This connecting wire 52 may be a separate component, which would have a first end 62 of the wire to conform to the male connector end 16, having the identical anode and cathode terminals 54, 56, with a second end 64 conforming to the female connector end 30, having identical heat element contacts 27a, 27b. In a second embodiment, the connecting wire 52 may be a permanent attachment to the base-power unit 12 and the fragrance dispersing unit 20, and could be retractable within either the unit components. Modification of either the base-power unit 12 of the fragrance dispersing unit 20 from the embodiments shown in the drawings would be required if the retractable wire embodiment is incorporated into the invention.

In operation a user places the automobile air freshener 10 inside an automobile. The user can select from any of three power sources using the power selector switch 32. If the user elects to use the vehicle cigarette lighter, the base power unit 12 is inserted into the cigarette lighter of the vehicle until the socket cathode contact 14 and the socket anode contact 18 make electrical contact with the corresponding components inside the cigarette lighter. A gel-scented cartridge 25 is then placed within the cartridge slot 24. Once electrical contact is made between the base power unit 12 and the vehicle's cigarette lighter, the electric heat element 26 begins warming. This causes heat to be dissipated to the heat dispersing plate 28, causing the gel-scented cartridge 25 to be warmed. Upon warming, the gel-scented cartridge 25 releases scent into the air in the automobile. Alternatively, a user may select the battery power position on the base power unit 12. In that case, the user must have inserted an appropriately sized battery, probably a double "A" sized cell. The same effect occurs when the battery power is selected. As another alternative, a user may select the solar power position on the base power unit 12. When the solar power position is selected, the base power unit must be placed in a position so that the solar cell 60 receives sufficient light to power the unit.

If the user desires to separate the base power unit from the fragrance unit, the connector wire 52 must be utilized. In that case, the first end 62 is placed over the male connector 16 and the base power unit 12. The second end 64 is then placed within the female connector end 30 of the fragrance unit. Again, the fragrance unit 20 and the base power unit 12 can be placed in different locations. As shown with the attached clips, the vent clips 50, the vented fragrance unit 20 can be removably clipped to an automobile vent port 48. This allows the scent escaping from the fragrance unit 20 to more thoroughly be distributed throughout the interior of the vehicle.

Thus having described the field of the invention, the prior art, the attached drawings, the summary of the invention, and the detailed description of the preferred embodiments, I claim:

1. An air freshener for use in an automobile, the freshener having a base power unit and a fragrance unit electrically connected to the base power unit, the fragrance unit having a heating element defining a longitudinal cartridge slot therein for receiving a scent cartridge, the heating element being in thermal communication with the longitudinal cartridge slot for warming the scent cartridge such that when power is supplied from the base power unit, the heating element is warmed, subsequently warming the scent cartridge, which disperses scent throughout the interior of a vehicle in which the freshener is deployed, wherein the improvement of the base power unit comprises:

a. a cigarette lighter adapted to be removably received within a cigarette lighter socket within a vehicle to draw power therefrom;

b. a battery compartment defined in the base power unit for receiving at least one dry cell battery to provide an alternate source of power;

c. solar panels exposed on an exterior surface of the base power unit for converting sunlight into electrical energy as another alternative power source;

d. a selector switch means for allowing a user to choose between any of the above three power sources so that the user can select the power source best adapted for the particular application;

e. a low voltage wire with connection means adapted to electrically connect the fragrance unit to the base power unit so that they can be spaced apart some distance; and f. a clip means for attaching the fragrance unit to an air vent in a vehicle in which the air freshener is deployed.

2. The air freshener of claim 1, having a retraction means disposed within the base power unit for retractably receiving the low voltage wire when the fragrance unit and the base power unit are connected.

* * * * *